United States Patent [19]

Krstenansky

[11] Patent Number: 5,192,747
[45] Date of Patent: Mar. 9, 1993

[54] ANTICOAGULANT PEPTIDES

[75] Inventor: John L. Krstenansky, Cincinnati, Ohio

[73] Assignee: Merrell Dow Pharmaceuticals Inc., Cincinnati, Ohio

[21] Appl. No.: 803,666

[22] Filed: Dec. 3, 1991

Related U.S. Application Data

[63] Continuation of Ser. No. 416,336, Oct. 3, 1989, abandoned.

[51] Int. Cl.$^5$ .................... A61K 37/00; A61K 37/02; C07K 5/00; C07K 7/00
[52] U.S. Cl. ........................................ 514/15; 514/12; 514/13; 514/14; 530/328; 530/327; 530/326; 530/324
[58] Field of Search .................. 514/12, 13, 14, 15; 580/326, 324, 328, 327, 330

[56] References Cited

U.S. PATENT DOCUMENTS

| | | | |
|---|---|---|---|
| 4,654,302 | 3/1987 | Fritz et al. | 435/70 |
| 4,668,662 | 5/1987 | Tripler et al. | 514/12 |
| 4,745,177 | 5/1988 | Fritz et al. | 530/324 |
| 4,767,742 | 8/1988 | Dodt et al. | . |
| 4,791,100 | 12/1988 | Krammer et al. | . |
| 4,832,849 | 5/1989 | Cardin | 210/635 |
| 4,929,602 | 5/1990 | Harker et al. | 514/18 |

FOREIGN PATENT DOCUMENTS

| | | |
|---|---|---|
| 171024 | 2/1986 | European Pat. Off. . |
| 0276014 | 7/1988 | European Pat. Off. . |
| 0291981 | 11/1988 | European Pat. Off. . |
| 0291982 | 11/1988 | European Pat. Off. . |
| 0347376 | 12/1989 | European Pat. Off. . |

OTHER PUBLICATIONS

Krstenansky, J. L., et al., Thrombosis Research 54, 319–325 (1989).
Cram, D. J., et al., Organic Chemistry, 2nd Edition, McGraw Hill, p. 609 (1964).
Owen, T. J., et al., J. Med. Chem., 31, 1009–1011 (1988).
Minar, E., et al., Klin Wochenschr Feb 15;63(4): 190–1 (1985).
Markwardt, F., et al., Thromb. Haemostasis, 52(2), 160–63 (1984).
Markwardt, F., et al., Thromb Haemost Jun. 28; 47(3):226–9 (1982).
Markwardt, F., et al., Thromb Haemost Jun. 28; 49(3):235–7 (1983).
Bajusz, S., et al., Proc. 18th European Peptide Symposium, 473–476 (1984).
Krstenansky et al., Biochim. Biophys. Acta 957, 53–59 (1988).
Sturzebecher, The Thrombin (R. Machovich, Ed.) vol. 1, 131–160, CRC Press, Boca Roton, Fla. (1984).
Hruby, V., Life Sciences 31, 189–199 (1982).
Mao, S. J. T., et al., Biochemistry 27, 8170–8173 (1988).
Maraganore, J. M., et al., J. Biol. Chem. 264(15), 8692–8698 (1989).
S. Bajusz, et al., Peptides 32, 473 (1984).
Chemical Abstracts 52:21222 abstracting F. Markwardt, Z. Physiol. Chem. 306, 147–56 (1957).
J. Dodt, et al., FEBS Letters 165(2), 180–84 (1984).
J–y Chang, FEBS Letters 164(2), 307–13 (1983).
Derwent Abstract 86-162807. W. German Patent Application No. 3445532, published Jun. 19, 1986, C. Plantorgran, inventor.
Derwent Abstract 86-162802/26. W. German Patent Application No. 3445517, published Jun. 19, 1986, Gen-Bio Tec Ges Gen, assignee.
J. Dodt, et al., Biol. Chem. Hoppe-Seyler 366, 379–385 (1985).
D. Bragdy, et al., Methods Enzymol., 45(Proteolytic Enzymes, Pt. B), pp. 674–675 (1976).
M. J. P. Pilat et al., Federation PRoc. 45(6), 1494, 76th Annual Meeting, ASBC Jun. 8–12, 1986.
J. L. Krstenansky et al., FEBS Letters 211(1) 10–16 (1987).
S. J. T. Mao, et al., Anal. Biochem. 161, 514–18, (1987).
R. P. Harvey, et al., Analytical Biochemistry, 161, 514–518 (1978).
J. L. Krstenansky, et al., J. Med. Chem. 30(9), 1688–1691.
J. L. Krstenansky, et al., Thrombosis Research 54, 319–325 (1989).
Krstenansky et al., Anticoagulant Peptides: . . . , J. Med. Chem., 1984, 30, 1688–1691.

*Primary Examiner*—Merrell C. Cashion, Jr.
*Assistant Examiner*—A. M. Davenport
*Attorney, Agent, or Firm*—Kenneth J. Collier

[57] ABSTRACT

The invention relates to peptide derivatives which are useful anticoagulant agents.

34 Claims, No Drawings

ANTICOAGULANT PEPTIDES

This is a continuation, of application Ser. No. 07/416,336, filed Oct. 3, 1989 and now abandoned.

This invention relates to novel anticoagulant peptides and as such are also valuable reagents to the development of anticoagulants.

BACKGROUND OF INVENTION

Anticoagulants are useful therapeutic agents in the pharmacological treatment of, for example, acute deep venous thrombosis, pulmonary embolism, acute arterial embolization of the extremities, myocardial infarction, and disseminated intravascular coagulation. Prophylactic administration of anticoagulants is believed to prevent a recurrence of embolism in patients with rheumatic or arteriosclerotic heart disease and to prevent certain thromboembolic complications of surgery. Administration of anticoagulants has also been indicated in the treatment of coronary artery and cerebrovascular disease. Arterial thrombosis, particularly in arteries supplying the heart muscle and brain, is a leading cause of death.

Hirudin is a 65 residue polypeptide isolated from the salivary glands of leeches. It is an anticoagulant agent, which is a thrombin specific inhibitor. Although quite potent, clinical use of hirudin isolated from leech extracts seems unlikely because of its limited quantity, expense, and allergic reactions which commonly follow administration of any foreign protein of this size.

Originally, applicants discovered a specific region of hirudin that is responsible, at least in part, for its anticoagulant activity. The peptide region (amino acid 55 to 65 of Hirudin) was chemically synthesized and shown to bind the recognition site of thrombin; the recognition site being spatially distinct from the the enzymatic cleavage site. Binding of synthetic peptides were also shown to competitively prevent binding of fibrinogen to the recognition site of thrombin, an important prerequisite to fibrin production and clot formation, and are thereby of potential medical value as anticoagulants.

Applicants have further prepared derivatives of this peptide containing single amino acid deletions of the basic sequence. Specifically, this series of amino acid deletions, taken in total, define the extent of sequence dependency of the peptide, positionally and compositionally, and provide the basis for extended rational drug design. Many of the peptide analogs of this type have attributes of the parent peptide and therefore may also serve as a scientifically interesting and therapeutically significant adjunct to anticoagulant therapy. Moreover, the amino acid analogs may in themselves contain enhanced potency and extended duration of action.

SUMMARY OF THE INVENTION

Peptide derivatives of the formula

X-$A_1$-$A_2$-$A_3$-$A_4$-$A_5$-$A_6$-$A_7$-$A_8$-$A_9$-$A_{10}$-Y wherein

X is an amino terminal residue selected from hydrogen, one or two alkyl groups of from 1 to 10 carbon atoms, one or two acyl groups of from 2 to 10 carbon atoms, carbobenzyloxy or t-butyloxy carbonyl;

$A_1$ is sequences of hirudin or its natural variants or portions thereof, a bond, or is a peptide containing from 1 to 11 residues of any amino acid;

$A_2$ is Phe, SubPhe, pChloroPhe, Pgl, Tha, His, Nap, $\beta$-(2- and 3-thienyl)alanine, $\beta$-(2-and 3-furanyl)alanine, $\beta$-(2-, 3-, and 4-pyridyl)alanine, $\beta$-(benzothienyl-2- and 3-)alanine, $\beta$-(1- and 2-naphthyl)alanine, Tyr, I-Tyr, or Trp;

$A_3$ is a bond, or is Glu, Asp, or Ala;

$A_4$ is a bond, or is any amino acid;

$A_5$ is a bond, or is Ile, Val, Leu, Nle, Phe, Ala;

$A_6$ is a bond, or is Pro, Hyp, 3,4-dihydroPro, thiazolidine-4-carboxylate, Sar, NMePgl, Azt, Pip, or D-Ala;

$A_7$ is a bond, or is any L-amino acid;

$A_8$ is a bond, or is any L-amino acid;

$A_9$ is a Tyr, I-Tyr, D-Tyr, His, Ala, Met, Trp, Phe, Leu, Nle, Ile, Val, Cha and Pro or is a dipeptide containing at least one of these amino acids or lipophilic amino acids;

$A_{10}$ is sequences of hirudin or its natural variants or portions thereof, a bond, or is a peptide containing from 1 to 11 residues of any amino acid;

Y is a carboxy terminal residue selected from OH, ($C_1$-$C_8$) alkoxy, amino, or mono di ($C_1$-$C_4$) alkyl substituted amino acids;

are useful anticoagulant agents and where at least one of the positions in $A_3$ through $A_8$ is a bond.

DETAILED DESCRIPTION OF THE INVENTION

The following common abbreviations of; (1) amino acids and their three letter code, (2) modified and unusual amino acids, and (3) terminal amino and carboxy substituents used throughout this specification:

(1): THE AMINO ACIDS AND THEIR THREE LETTER CODE

| L-AMINO ACIDS | D-AMINO ACIDS |
|---|---|
| Ala (or A) — alanine | D-Ala (or a) — D-alanine |
| Arg (or R) — arginine | D-Arg (or r) — D-arginine |
| Asn (or N) — asparagine | D-Asn (or n) — D-asparagine |
| Asp (or D) — aspartic acid | D-Asp (or d) — D-aspartic acid |
| Cys (or C) — cysteine | D-Cys (or c) — D-cysteine |
| Gly (or G) — glysine | D-Glu (or e) — D-glutamic acid |
| Glu (or E) — glutamic acid | D-Val (or v) — D-valine |
| Val (or V) — valine | D-Gln (or q) — D-glutamine |
| Gln (or Q) — glutamine | D-His (or h) — D-histidine |
| His (or H) — histidine | D-Ile (or i) — D-isoleucine |
| Ile (or I) — isoleucine | D-Leu (or l) — D-leucine |
| Leu (or L) — leucine | D-Lys (or k) — D-lysine |
| Lys (or K) — lysine | D-Phe (or f) — D-phenylalanine |
| Phe (or F) — phenylalanine | D-Met (or m) — D-methionine |
| Met (or M) — methionine | D-Pro (or p) — D-proline |
| Pro (or P) — proline | D-Ser (or s) — D-serine |
| Ser (or S) — serine | D-Thr (or t) — D-threonine |
| Thr (or T) — threonine | D-Trp (or w) — D-tryptophan |
| Trp (or W) — tryptophan | D-Tyr (or y) — D-tyrosine |
| Tyr (or Y) — tyrosine | |

(2): MODIFIED AND UNUSUAL AMINO ACIDS

Aba—$\alpha$-amino-n-butyric acid
pClPhe—para-chloro-phenylalanine
Cha—cyclohexylalanine
Chg—cyclohexylglycine
Hyp—hydroxyproline
I-Tyr—3-idodotyrosine, 5-iodotyrosine, 3,5-diiodotyrosine,
YMeGlu—D-glutamic acid gamma methyl ester NMePhe—N-methyl phenylalanine
NMePgl—N-methyl phenylglycine
Npa—β-(naphthyl)alanine
3,4-dihydroPro—3,4-dihydroproline
pNO₂Phe—para-nitro-phenylalanine
Nle—norleucine
Orn—ornithine
Pip—pipecolate
Pba—p-aminophenyl butric acid
pSubPhe—para substituted phenylalanine
Pgl—phenylglycine
Sar—sarcosine (N-methylglycine)
SubPhe—ortho, meta, or para, mono- or di- substituted phenylalanine
Tha—β-(2-thienyl)-alanine
Tiq—Tetrahydroisoquinoline 3-carboxylate

AMINO AND CARBOXY TERMINAL ACID SUBSTITUENTS

Ac—acetyl
Azt—azetidine-2-carboxylate
Cin—cinnamoyl
3,4-dihydroCin—3,4-dihydrocinnamoyl
Glt—glutaryl
Mal—maleyl
Oac—8-aminooctanoic acid
Oct—n-octyl
Suc—succinyl
Glt—glutaryl
Tfa—trifloroacetyl
—C-terminal amide The following designates the known naturally occurring amino acid sequence variations of Hirudin:

AMINO ACID SEQUENCE VARIATIONS OF HIRUDIN 1 2 3 4 5 6 7 8 9 10 11 12 13 14
Val Val Tyr Thr Asp Cys Thr Glu Ser Gly Gln Asn Leu Cys
                                              Ile Thr 15 16 17 18 19 20 21 22 23 24 25 26 27 28
Leu Cys Glu Gly Ser Asn Val Cys Gly Gln Gly Asn Lys Cys
                                                    Lys 29 30 31 32 33 34 35 36 37 38 39 40 41 42
Ile Leu Gly Ser Asp Gly Glu Lys Asn Gln Cys Val Thr Gly
            Asn        Lys Gly
            Gln             Asp 43 44 45 46 47 48 49 50 51 52 53 54 55 56
Glu Gly Thr Pro Lys Pro Glx Ser His Asn Asp Gly Asp Phe
                      Asn     Glu 57 58 59 60 61 62 63 64 65
Glu Glu Ile Pro Glu Glu Tyr Leu Gln
    Pro          Asp     Asp Glu
            (Ala⁶³ Tyr⁶⁴ Leu/Asp⁶⁴ Glu⁶⁵)

Definitions in the Invention

The naturally occurring amino acids, with the exception of glycine, contain a chiral carbon atom. Unless otherwise specifically indicated, the optically active amino acids, referred to herein, are of the L-configuration. For example, any of the amino acids of the $A_1$ or $A_{10}$ group can be of the D- or L-configuration. As is customary, the structure of peptides written out herein is such that the amino terminal end is on the left side of the chain and the carboxy terminal end is on the right side of the chain.

An alkyl group and the alkyl portion of an alkoxy group is taken to include straight, branched, or cyclic alkyl groups, for example, methyl, ethyl, propyl, isopropyl, butyl, isobutyl, tert-butyl, pentyl, isopentyl, sec-pentyl, cyclopentyl, hexyl, isohexyl, cyclohexyl and cyclopentyl-methyl, heptyl, octyl(Oct), 8-aminooctanoic acid(Oac). An acyl group of from 2 to 10 carbon atoms is taken to include straight, branched, cyclic, saturated and unsaturated acyl groups having 1 or 2 carbonyl moieties per group, for example, acetyl(Ac), azetidine-2-carboxylate(Azt), benzoyl succinyl, cinnamoyl(Cin), 3,4-dihydrocinnamoyl(3,4-dihydroCin), maleyl(Mal), and glutaryl(Glt). Both alkyl and acyl substituents are taken to include those groups with halogen substituents, were a halogen group is a fluoro, chloro, bromo or iodo, for example, trifloroacetyl(Tfa).

The term "any amino acid" as used herein does not purport to include any carboxylic acid having an amino substituent, but rather is used as it is commonly used by those skilled in the art of polypeptide derivatives and includes the naturally occurring amino acids as well as other "non-protein" α-amino acids commonly utilized by those in the peptide chemistry arts when preparing synthetic analogs of naturally occurring peptides. The naturally occurring amino acids are the "L-amino acids" glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine, ornithine, and lysine. Also included as "any amino acid" would be the D-isomers ("D-amino acids") of the naturally occurring L-amino acids; D-alanine, D-valine, D-leucine, D-isoleucine, D-serine, D-methionine, D-threonine, D-phenylalanine, D-tyrosine, D-tryptophan, D-cysteine, D-proline, D-histidine, aspartic acid, D-asparagine, D-glutamic acid, D-glutamine, D-arginine. Also included are "non-protein" α-amino acids, examples are norleucine, norvaline, alloisoleucine, homoarginine, thiaproline, dihydroproline, hydroxyproline (Hyp), homoserine, cyclohexylglycine (Chg), α-amino-n-butyric acid (Aba), cyclohexylalanine (Cha), aminophenylbutyric acid (Pba), phenylalanines mono or di-substituted at the ortho, meta, or para positions, such as para substituted phenylalanine (pSubPhe) and para-chlorophenylalanine, and para-nitrophenylalanine (pNO₂Phe) or positions of the phenyl moiety with one or two of the following, a ($C_1$–$C_4$) alkyl, ($C_1$–$C_4$) alkoxy, halogen, or nitro groups or substituted with a methylenedioxy group, β-2- and 3-thienylal-alanine, β-2- and 3-furanylalanine, β-2-, 3-, and 4-pyridylalanine, β-(benzothienyl-2- and 3-yl)alanine, β-(1-and 2-naphthyl)alanine(Npa), O-alkylated derivates of serine, threonine, or tyrosine, methyl esters of glutamic and aspartic acid, S-alkylated cysteine, the O-sulfate ester of tyrosine, and halogenated tyrosines such as 3-idodotyrosine, 5-iodotyrosine, 3,5-diiodotyrosine.

By the expression "sequences of hirudin or its natural variants" applicants intend that the amino acid sequences found for hirudin in nature apply.

The term "portions thereof" of Hirudin and its variants is meant to include a consecutive region of 4 amino acids derived from the sequence of hurudin or its variants.

The term "lipophilic amino acid" includes Tyr, Phe, Leu, Met, Nle, Ile, Val, and Pro. Further, the term "imino acids" is meant to include all N-alkyl amino acids. Examples of imino acids would be N-methyl phenylalanine (NMePhe), N-methyl phenylglycine (NMePgl), 2,4-dihydroproline (3,4-dihydroPro), p-aminophenyl butyric acid (Pba), sarcosine (Sar), and Proline (Pro), pipecolate (Pip). The expression "a peptide containing from 1-11 residues of any amino acid" is meant to reflect that addition of amino acids to either the amino or carboxy terminal of the core amino acids ($A_2$–$A_9$) encompase the core structure with its intrinsic activity.

The polypeptides of formula 1 can form pharmaceutically acceptable salts with any non-toxic, organic or inorganic acid. Illustrative inorganic acids which form suitable salts include hydrochloric, hydrobromic, sulphuric and phosphoric acid and acid metal salts such as sodium monohydrogen orthophosphate and potassium hydrogen sulfate. Illustrative organic acids which form suitable salts include the mono, di and tricarboxylic acids. Illustrative of such acids are, for example, acetic, glycolic, lactic, pyruvic, malonic, succinic, glutaric, fumaric, malic, tartaric, citric, ascorbic, maleic, hydroxymaleic, benzoic, hydroxybenzoic, phenylacetic, cinnamic, salicylic, 2-phenoxybenzoic and sulfonic acids such as methane sulfonic acid and 2-hydroxyethane sulfonic acid. Salts of the carboxy terminal amino acid moiety include the non-toxic carboxylic acid salts formed with any suitable inorganic or organic bases. Illustratively, these salts include those of alkali metals, as for example, sodium and potassium; alkaline earth metals, such as calcium and magnesium; light metals of Group IIIA including aluminum; and organic primary, secondary and tertiary amines, as for example, trialkylamines, including triethylamine, procaine, dibenzylamine, 1-ethenamine, N,N'-dibenzylethylenediamine, dihydroabietylamine, N-(lower)alkylpiperidine, and any other suitable amine.

As with any generic group of chemical compounds, certain groups are preferred. Applicants prefer those peptide derivatives of formula 1 wherein
X is hydrogen, acetyl, or succinyl.
$A_1$ is a bond or is Hirudin or its natural variants inclusive of amino acids 1 to 54 or regions thereof, or a bond;
$A_2$ is a bond or is Tyr, Trp, Glu, His, Leu, Phe, D-Phe, SubPhe, pChloroPhe, NMephe, Tha, 3,4-dihydroCin, Cin, Nap, β-(2- and 3-thienyl)alanine, β-(2-and 3-furanyl)alanine, β-(2-, 3-, and 4-pyridyl)alanine, β-(benzothienyl-2- and 3-yl alanine, or β-(1- and 2-naphthyl)alanine;
$A_3$, is a bond, or Glu, Ala;
$A_4$, is a bond, or Glu, Asp, Pro, Ala, Azt, Pip, imino acid or D-amino acid;
$A_5$, is a bond, or Ile, Leu;
$A_6$, is a bond, or Pro, Sar, D-Ala, Hyp or NMePgl;
$A_7$, is a bond, or Glu, Gln, Asp or Ala;
$A_8$, is a bond, or Glu, Asp or Ala;
$A_9$, is a bond, or Ala, Pro, Cha, or the dipeptide Ala-Tyr, Tyr-Leu, Ala-Phe, Tyr-Tyr, Ala-Leu, Tyr-Ala, Glu-Leu, D-Tyr-Leu, Leu-Phe, Sar-Cha, Pro-Cha, Cha-Leu, Ala-Cha, Tyr-Cha;
$A_{10}$, is a bond, or yMeGlu, Glu, D-Glu, Asn, D-Asn, Asn-ol, Pro, Gln, Ala, Lys, D-Lys, Asp, Orn, Asp, or is Ala; and
Y is a carboxy terminal residue selected from OH, ($C_1$–$C_8$) alkoxy, amino, mono or di ($C_1$–$C_4$) alkyl substituted amino acids, or is an alcohol terminal residue;
where at least one of the positions in $A_3$ through $A_9$ is a bond.
Especially preferred are those peptide derivatives of formula 1 wherein either;
X, is Suc, Mal;
$A_1$, is a bond;
$A_2$, is Tyr, Phe, Nap;
$A_3$, is Glu, or is bond;
$A_4$, is Glu, Pro, Tiq, or is bond;
$A_5$, is Ile, or is bond;
$A_6$, is Pro, or is bond;
$A_7$, is Glu, or is bond;
$A_8$, is Glu, or is bond;
$A_9$, is Ala-Cha, Tyr-Leu, Ala, Cha;
$A_{10}$, is Gln, D-Glu, Asn; and
Y is OH, $NH_2$.
where at least one of the positions in $A_3$ through $A_8$ is a bond.

Synthesis:

The proteins of this invention can be prepared by a variety of procedures readily known to those skilled in the art. Such procedures include solution phase peptide synthesis, the solid phase sequential and block synthesis, gene cloning and combinations of these techniques. The solid phase sequential procedure can be performed using established automated methods such as by use of an automated peptide sythesizer. In this procedure, the peptides were constructed on the resin beginning with the C-terminal protected amino acid. The resin support employed can be any suitable resin conventionally employed in the art for the solid phase preparation of polypeptides, preferably polystyrene which has been cross-linked with 0.5 to about 3 percent divinyl benzene, which has been either chloromethylated or hydroxymethylated to provide sites for ester formation with the initially introduced α-amino protected amino acid. For C-terminal amides, a pimethylbenzhydrylamine resin can be used. After completion of coupling of the sequence either the Boc protecting group was removed or left in place or it was removed and the N-terminal amino group acylated. Displacement of the protected fragment from the resin was accomplished using the appropriate amino alcohol.

An example of a hydroxymethyl resin is described by Bodanszky et al., *Chem. Ind. (London)* 38, 1597–98 (1966). A chloromethylated resin is commercially available from Bio Rad Laboratories, Richmond, Calif., and the preparation of such a resin is described by Stewart et al., "Solid Phase Peptide Synthesis" (Freeman & Co., San Francisco 1969), Chapter 1, pp. 1–6. The protected amino acid can be bound to the resin by the procedure of Gisin, *Helv. Chem Acta*, 56, 1476 (1973). Many resin bound, protected amino acids are commercially available. As an example, to prepare a polypeptide of this invention wherein the carboxy terminal end is a D.Glu residue, a tert-butyloxycarbonyl (Boc) protected D.Glu bound to a benzylated, hydroxymethylated phenylacetamidomethyl (PAM) resin can be used.

Following the coupling of the α-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethan type protecting groups such as benzyloxycarbonyl and substituted benzyloxycarbonyl, such as p-chlorobenzyloxycarbonyl, p-nitrobenzyl- carbonyl, p-bromobenzyloxycarbonyl, p-methoxybenzyloxycarbonyl, 1-(p-biphenylyl)-1-methylethoxycarbonyl, α, α-dimethyl-3,5-dimethoxybenzyloxycarbonyl and benzhydryloxycarbonyl; (3) aliphatic urethan protecting groups such as tertbutyloxycarbonyl (Boc), diisopropylmethoxycarbonyl, isopropyloxycarbonyl, ethoxycarbonyl and allyloxycarbonyl; (4) cycloalkyl urethan type protecting groups such as cyclopentyloxycarbonyl, adamantyloxycarbonyl and cyclohexyloxycarbonyl; (5) thiourethan type protecting groups such as phenylthiocarbonyl; and (6) alkyl type protecting groups such as triphenylmethyl (trityl) and benzyl. The preferred α-amino protecting group is tert-butyloxycarbonyl.

As is known in the art of solid phase peptide synthesis many of the amino acids bear functionalities requiring protection during the chain preparation. The use and selection of the appropriate protecting group is within the ability of those skilled in the art and will depend upon the amino acid to be protected and the presence of other protected amino acid residues on the peptide. The selection of such a side chain protecting group is critical in that it must be one which is not removed by cleavage during cleavage of the protecting group of the u-amino moiety. For example, suitable side chain protecting groups for lysine are benzyloxycarbonyl and substituted benzyloxycarbonyl, said substituent being selected from halo (e.g., chloro, bromo, fluoro) and nitro (e.g., 2-chlorobenzyloxycarbonyl, p-nitrobenzyloxy-carbonyl, 3,4-dichlorobenzyloxycarbonyl), tosyl, t-amyloxycarbonyl, t-butyloxycarbonyl and diisopropylmethoxycarbonyl. The alcoholic hydroxyl group of threonine and serine can be protected with an acetyl, benzoyl, tert-butyl, trityl, benzyl, 2,6-dichlorobenzyl or benzyloxycarbonyl group. The preferred protecting group is benzyl.

The selection of an appropriate coupling reagent is within the skill of the art. A particularly suitable coupling reagent where the amino acid to be added is Gln, Asn or Arg is N,N'-diisopropylcarbodiimide and 1-hydroxybenzotriazole. The use of these reagents prevents nitrile and lactam formation. Other coupling agents are (1) carbodiimides (e.g., N,N'-dicyclohexylcarbodiimide and N-ethyl-N'-(Y-dimethylaminopropyl-carbodiimide); (2) cyanamides (e.g., N,N-dibenzylcyanamide); (3) ketenimines; (4) isoxazolium salts (e.g., N-ethyl-5-phenyl-isoxazolium-3'-sulfonate; (5) monocyclic nitrogen containing heterocyclic amides of aromatic character containing one through four nitrogens in the ring such as imidazolides, pyrazolides, and 1,2,4-triazolides. Specific heterocyclic amides that are useful include N,N'-carbonyldiimidazole and N,N-carbonyl-di-1,2,4-triazole; (6) alkoxylated acetylene (e.g., ethoxyacetylene); (7) reagents which form a mixed anhydride with the carboxyl moiety of the amino acid (e.g., ethylchloroformate and isobutylchloroformate) or the symmetrical anhydride of the amino acid to be coupled (e.g., Boc-Ala-O-Ala-Boc), (8) nitrogen containing heterocyclic compounds having a hydroxy group on one ring nitrogen (e.g., N-hydroxyphthalimide, N-hydroxysuccinimide and 1-hydroxybenzotriazole) and (9) Castro's Reagent (BOP). Other activating reagents and their use in peptide coupling are described by Kapoor, J. Pharm. Sci., 59, pp. 1–27 (1970). Applicants prefer the use of the symmetrical anhydride as a coupling reagent for all amino acids except Arg, Asn and Gln.

Each protected amino acid or amino acid sequence is introduced into the solid phase reactor in about a four-fold excess and the coupling is carried out in a medium of dimethylformamide: methylene chloride (1:1) or in dimethylformamide alone or preferably methylene chloride alone. In cases where incomplete coupling occurs, the coupling procedure is repeated before removal of the α-amino protecting group, prior to the coupling of the next amino acid in the solid phase reactor. The success of the coupling reaction at each stage of the synthesis is monitored by the ninhydrin reaction as described by E. Kaiser et al, Analyt. Biochem. 34, 595 (1970).

Following the coupling of the u-amino protected amino acid to the resin support, the protecting group is removed using any suitable procedure such as by using trifluoroacetic acid in methylene chloride, trifluoroacetic acid alone, or HCl in dioxane. The deprotection is carried out at a temperature of between 0° C. and room temperature. Other standard cleaving reagents and conditions for removal of specific α-amino protecting groups may be used. After removal of the α-amino protecting group the other amino protected amino acids are coupled step-wise in the desired order. Alternatively, multiple amino acid groups may be coupled by the solution method prior to coupling with the resin supported amino acid sequence.

After the desired amino acid sequence has been obtained, the peptide is removed from the resin and deprotected. This can be done by hydrolysis such as by treatment of the resin bound polypeptide with anhydrous liquid HF in the presence of scavengers (e.g. amisole). Typically protecting group removal is done after the peptide chain synthesis is complete but the protecting groups can be removed at any other appropriate time.

Purification and analysis of the deprotected peptide is accomplished by a number of standard procedures. The selection of the appropriate purification and analysis procedures is within the skill of the art. A suitable purification procedure is preparative HPLC. Analysis of the purified peptides can be done by analytical HPLC, amino acid analysis, fast atom bombardment mass spectrometry, and any other suitable means of analysis.

Therapeutic Use:

The anticoagulant dose of an peptide derivative of this invention is from 0.2 mg/kg to 250 mg/kg of patient body weight per day depending on the patient, the severity of the thrombotic condition to be treated and the peptide derivative selected. The suitable dose for a particular patient can be readily determined. Preferably from 1 to 4 daily doses would be administered typically with from 5 mg to 100 mg of active compound per dose. The amount of a peptide of this invention required to inhibit or prevent blood coagulation in an extracorporeal medium such as stored whole blood can be readily determined by those skilled in the art.

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats and mice. Inhibition of blood coagulation is useful not only in anticoagulant therapy of individuals having thrombotic conditions, but is useful whenever inhibition of blood coagulation is desirable, such as to prevent coagulation in stored whole blood and to prevent coagulation in other biological samples for testing or storage.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

The compounds can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber manufactured by the Dow-Corning Corporation.

EXAMPLES

This invention is illustrated by the following, nonlimiting examples.

EXAMPLE 1

Preparation of Anticoaqulant Peptides.

The peptide was synthesized by solid-phase methods using 8.3 mmol of a 0.56 mmol/g Bod D-Glu(Bzl) Merrifield resin on a Vega semi-automated peptide synthesizer. Single symmetrical anhydride couplings were performed with 18.3 mmol Nα-Boc-amino acid (Peptides International), except in the case of Boc-Cha which required two coupling reactions to give a negative Kaiser test. Portions of the peptide resin (0.7 to 1.5 g) were removed and set aside after cycles 3 through 8; for des-Glu$^{57}$ 1.36 g (0.50 mmol) of Boc-Pro-Ile-Pro-Glu(Bzl)-Glu(Bzl)-Ala-Cha-D-Glu(Bzl) Merrifield resin was reserved after cycle 8. The protected peptide fragment resin was transfered to an applied Biosystems reaction vessel where Boc-Tyr(2-BrZ) was added using double symmetrical anhydride coupling with 2.0 mmol amino acid. The Nα-Boc protection was removed with 50% trifluoroacetic acid in methylene chloride, neutralized with three washings of 10% diisopropylethylamine in methylene chloride, washed three times with methylene chloride, and dried under nitrogen flow. The peptide was Nα succinylated with double succinic anhydride coupling in dimethyl formamide, rinsed three times with dimethyl formamide, neutralized with two washes of 10% diisopropylethylamine in methylene chloride, washed three times with methylene chloride and dried in vacuo. The peptide was deprotected and cleaved from the resin with anhydrous HF containing 5% anisol at 0° C. for 60 min. The HF was removed in vacuo at 0° C.; the peptide was extracted from the resin with 25% aqueous acetonitrile, frozen and lyophilized.

Preparative HPLC was performed on a $C^{18}$ Beckman 50.8×150 mm column with a 29.6–31.6% acetonitrile linear gradient over 15 min in 0.1% aqueous trifluoroacetic acid at 80 ml/min. The major peak (monitored at 280 nm) was collected and lyophilized yeilding 281 mg of the desired product. Homogeneity was determined by HPLC: Vydac 218TP54 (4.6×250 mm) $C^{18}$ column, 2.0 ml/min, $t_0=1.5$ min, time of elution with a 15–40% acetonitrile linear gradient over 25 min to 0.1% trifluoroacetic acid is 17.1 min.

Analysis of purified labeled peptides gave the desired molecular ion peak by FAB-MS and had an amino acid analysis in accordance with the desired peptide. In this way the following peptides have the stated physical properties specified below.

Samples were tested in a thrombin induced fibrin clot inhibition assay. All the solutions of the assay were made with an assay buffer containing 0.12M sodium chloride, 0.01M sodium phosphate, 0.01% sodium azide and 0.1% bovine serum albumin, pH 7.4. Bovine thrombin was titrated to an appropriate concentration so that fibrin clot formation could be monitored by a microtiter plate reader (Bio-Tek EL 309) within 60 min at 405 nm. This solution of thrombin (50 ul; 0.2 pmol) was added to the wells of a microtiter plate containing 50 ul of a solution of the synthetic peptide being tested. After 1 min agitation and an additional 10 mins incubation at 20° C., 100 ul of diluted plasma (1:10) in 0.1% EDTA was added and vortexed for 20 s. The turbidity of the solution was monitored by the autoreader at 5 min intervals. $IC_{50}$ is calculated from the results and is defined as the concentration of peptide which lead to half of the turbidity observed relative to a control containing no inhibitor. This is equivalent to a twofold increase in fibrin clot formation time. For the assays using human thrombin,, it and bovine thrombin were titrated to concentrations which gave the fibrin clot at the same rate over a 30 min period. In this way the following peptides have the stated biological properties for the examples specified below were + signifies an $IC_{50}>25$ uM and <200 μM, and ++ signifies an $IC_{50}<25$ μM.

---

1) Suc—Tyr—Pro—Ile—Pro—Glu—Glu—Ala—Cha—D-Glu OH
   MW 1200 FAB-MS (MH)$^+$ 1201
      Z(3)   Pro(2)   Ile(1)   Tyr(1)   Ala(1)
      3.08   1.97     0.96    0.99    0.99
   In vitro potency: +
2) H—Gly—Asp—Phe—Glu—Glu—Ile—Glu—Glu—Tyr—Leu—Gln—OH -continued

MW 1370 FAB-MS (MH)+ 1371

| Z(5) | Ile(1) | Tyr(1) | Gly(1) | B(1) | Phe(1) | Leu(1) |
|------|--------|--------|--------|------|--------|--------|
| 4.93 | 0.85 | 0.95 | 1.09 | 1.10 | 1.08 | 0.99 |

In vitro potency: +

3) Suc—Tyr—Glu—Pro—Tiq—Glu—Glu—Ala—Cha—D-Glu—OH
MW 1278 FAB-MS (MH)+ 1279

| Z(4) | Pro(1) | Ile(1) | Tyr(1) | Ala(1) | Cha(1) |
|------|--------|--------|--------|--------|--------|
| 4.05 | 0.93 | 0.96 | 0.95 | 1.03 | 1.03 |

In vitro potency: ++

4) Suc—Tyr—Glu—Pro—Ile—Pro—Glu—Glu—Ala—Gln—NH$_2$
MW 1158 FAB-MS (MH)+ 1175

| Z(4) | Pro(2) | Ile(1) | Tyr(1) | Ala(1) |
|------|--------|--------|--------|--------|
| 4.15 | 1.94 | 0.96 | 1.01 | 0.95 |

In vitro potency: ++

5) Suc—Tyr—Glu—Pro—Ile—Pro—Glu—Glu—Cha—Gln—NH$_2$
MW 1256 FAB-MS (MH)+ 1257

| Z(4) | Pro(2) | Ile(1) | Tyr(1) | Ala(1) |
|------|--------|--------|--------|--------|
| 4.15 | 1.98 | 0.91 | 0.97 | 1.05 |

In vitro potency: ++

6) Suc—Tyr—Glu—Pro—Ile—Pro—Glu—Ala—Cha—Asn—OH
MW 1184 FAB-MS (MH)+ 1185

| B(1) | Z(2) | Pro(2) | Ile(1) | Tyr(1) | Ala(1) |
|------|------|--------|--------|--------|--------|
| 1.02 | 2.09 | 1.98 | 0.93 | 1.01 | 0.97 |

In vitro potency: ++

7) Suc—Tyr—Glu—Pro—Ile—Pro—Glu—Ala—Cha—Asn—OH
MW 1161 FAB-MS (MH)+ 1162

| Z(3) | Pro(2) | Ile(1) | Tyr(1) | Ala(1) | B(1) |
|------|--------|--------|--------|--------|------|
| 3.14 | 1.95 | 0.95 | 1.00 | 0.96 | 1.01 |

In vitro potency: ++

8) Mal—Tyr—Pro—Ile—Pro—Glu—Glu—Ala—Cha—D-Glu—OH
MW 1198 FAB-MS (MH)+ 1198

| Z(4) | Pro(2) | Ile(1) | Tyr(1) | Ala(1) |
|------|--------|--------|--------|--------|
| 3.06 | 2.01 | 0.95 | 0.99 | 1.01 |

In vitro potency: +

9) Suc—Nap—Pro—Ile—Pro—Glu—Glu—Ala—Cha—D-Glu—OH
MW 1234 FAB-MS (MH)+ 1234

| Z(3) | Pro(2) | Ala(1) |
|------|--------|--------|
| 3.08 | 2.00 | 0.94 | 0.97 |

In vitro potency: ++

10) Suc—Tyr—Glu—Ile—Pro—Glu—Glu—Ala—Cha—D-Glu—OH
MW 1232 FAB-MS (MH)+ 1233

| Z(4) | Pro(1) | Ile(1) | Tyr(1) | Ala(1) |
|------|--------|--------|--------|--------|
| 4.07 | 0.99 | 0.96 | 0.98 | 0.99 |

In vitro potency: +

11) Suc—Tyr—Glu—Pro—Pro—Glu—Glu—Ala—Cha—D-Glu—OH
MW 1216 FAB-MS (MH)+ 1217

| Z(4) | Pro(2) | Tyr(1) | Ala(1) |
|------|--------|--------|--------|
| 4.05 | 1.97 | 0.98 | 1.00 |

In vitro potency: +

12) Suc—Tyr—Glu—Pro—Ile—Glu—Glu—Ala—Cha—D-Glu—OH
MW 1232 FAB-MS (MH)+ 1233

| Z(4) | Pro(1) | Ile(1) | Tyr(1) | Ala(1) |
|------|--------|--------|--------|--------|
| 4.10 | 1.01 | 0.94 | 0.96 | 0.99 |

In vitro potency: ++

13) Suc—Tyr—Glu—Pro—Ile—Pro—Glu—Ala—Cha—D-Glu—OH
MW 1200 FAB-MS (MH)+ 1201

| Z(3) | Pro(2) | Ile(1) | Tyr(1) | Ala(1) |
|------|--------|--------|--------|--------|
| 3.16 | 1.97 | 0.93 | 0.96 | 0.98 |

In vitro potency: ++

14) Suc—Tyr—Glu—Pro—Ile—Pro—Glu—Glu—Ala—D-Glu—OH
MW 1176 FAB-MS (MH)+ 1177

| Z(4) | Pro(2) | Ile(1) | Tyr(1) | Ala(1) |
|------|--------|--------|--------|--------|
| 4.08 | 1.97 | 0.96 | 0.99 | 1.00 |

In vitro potency: ++

15) Suc—Tyr—Glu—Pro—Ile—Pro—Glu—Glu—Cha—D-Glu—OH
MW 1258 FAB-MS (MH)+ 1259

| Z(4) | Pro(2) | Ile(1) | Tyr(1) |
|------|--------|--------|--------|
| 4.10 | 2.01 | 0.91 | 0.98 |

In vitro potency: ++

16) Suc—Tyr—Glu—Pro—Ile—Pro—Glu—Glu—Ala—Gln—OH
MW 1175 FAB-MS (MH)+ 1175

| Z(4) | Pro(2) | Ile(1) | Tyr(1) | Ala(1) |
|------|--------|--------|--------|--------|
| 4.11 | 1.98 | 0.93 | 1.01 | 0.97 |

In vitro potency: ++

17) Suc—Phe—Glu—Pro—Ile—Pro—Glu—Glu—Ala—Gln—NH$_2$
MW 1158 FAB-MS (MH)+ 1159

| Z(4) | Pro(2) | Ile(1) | Ala(1) | Phe(1) |
|------|--------|--------|--------|--------|
| 4.10 | 2.05 | 0.93 | 0.96 | 0.97 |

In vitro potency: +

18) Suc—Tyr—Glu—Pro—Ile—Pro—Glu—Glu—Ala—Cha—OH
MW 1200 FAB-MS (MH)+ 1201

| Glx(3) | Pro(2) | Ile(1) | Tyr(1) | Ala(1) |
|--------|--------|--------|--------|--------|

| -continued |      |      |      |      |
|------|------|------|------|------|
| 3.10 | 1.94 | 0.98 | 0.99 | 0.99 |

In vitro potency: ++
19) Suc—Glu—Pro—Ile—Pro—Glu—Glu—Ala—Cha—D-Glu—OH
MW 1166 FAB-MS (MH)+ 1167

| Glx(4) | Pro(2) | Ile(1) | Ala(1) |
|--------|--------|--------|--------|
| 4.12   | 1.95   | 0.96   | 0.98   |

In vitro potency: +

What is claimed is:

1. A peptide derivative of the formula

wherein;
X is an amino terminal substituent selected from hydrogen, one or two alkyl groups of from 1 to 10 carbon atoms, one or two acyl groups of from 2 to 10 carbon atoms, carbobenzyloxy or t-butyloxy carbonyl;
$A_1$ is a sequence of Gly-Asp, 1–11 amino acids of hirudin or natural variants of hirudin, or a bond;
$A_2$ is a bond or is Phe, SubPhe, pChloroPhe, D-Phe, NMePhe, Pgl, Tha, His, Cin, Nap, Leu, Gln, 3,4-dihydroCin, $\beta$-(2- and 3-thienyl)alanine, $\beta$-(2-and 3-furanyl)alanine, $\beta$-(2-, 3-, and 4-pyridyl)alanine, $\beta$-(benzothienyl-2- and 3-)alanine, $\beta$-(1- and 2-naphthyl)alanine, Tyr or Trp;
$A_3$ is a bond, Glu, or Asp;
$A_4$ is a bond, Pro, or Glu;
$A_5$ is a bond, or Ile;
$A_6$ is a bond, [Tiq, ]Pro, Hyp, 3,4-dihydroPro, thiazolidine-4-carboxylate, Sar, NMePgl, Azt, Pip;
$A_7$ is a bond, Glu, or asp;
$A_8$ is a bond, Glu, Asp, or Ala;
$A_9$ is a bond, or is a Tyr, I-Tyr, D-Tyr, Trp, Phe, Leu, Nle, Ile, Val, Ala, Cha or Pro or is a dipeptide containing at least one of these amino acids;
$A_{10}$ is a sequence of 1–11 amino acids of hirudin or natural variants of hirudin, D-Glu, Glu, Gln, Asn, or a bond;
Y is a carboxy terminal substituent selected from OH, $(C_1-C_8)$ alkoxy, amino, mono di $(C_1-C_4)$ alkyl substituted amino acids, or is an alcohol terminal residue; and where at least one of the positions in $A_3$ through $A_9$ is a bond.

2. An peptide derivative of claim 1 wherein $A_2$ is Tyr, Nap, or Phe

3. A peptide derivative of claim 1 wherein $A_3$ is a bond, or Glu.

4. A peptide derivative of claim 1 wherein $A_4$ is a bond, or Pro.

5. A peptide derivative of claim 1 wherein $A_5$ is a bond or Ile.

6. A peptide derivative of claim 1 wherein $A_6$ is a bond or Pro.

7. A peptide derivative of claim 1 wherein $A_7$ is Glu.

8. A peptide derivative of claim 1 wherein $A_8$ is a bond, Glu or Asp.

9. A peptide derivative of claim 1 wherein $A_9$ is Ala, Cha, Ala-Cha or Tyr-Leu.

10. A peptide derivative of claim 1 wherein $A_{10}$ is Gln, Asn, or D-Glu.

11. A peptide derivative of claim 1 wherein X is H, or $NH_2$.

12. A method of reducing blood coagulation in a patient in need thereof which comprises administering an anticoagulant effective amount of a peptide derivative of one of claims 1–11 and a pharmaceutically acceptable carrier.

13. A method of reducing blood coagulation in a medium which comprises contacting the medium with a blood coagulation effective amount of peptide of one of claims 1–11.

14. A peptide which is an analog of the naturally occurring Hirudins of one of claims 1–11 containing the binding site responsible for the binding to thrombin and therefore capable of acting as a competitive inhibitor of thrombin.

15. A compound of claim 1 of the structure Suc-Tyr-Pro-Ile-Pro-Glu-Glu-Ala-Cha-D-Glu-OH wherein X=Suc, $A_1$=a bond, $A_2$=Tyr, $A_3$=a bond, $A_4$=Pro, $A_5$=Ile, $A_6$=Pro, $A_7$=Glu, $A_8$=Glu, $A_9$=Ala-Cha, $A_{10}$=D-Glu, and Y is a carboxy terminal substituent that is OH.

16. A compound of claim 1 of the structure H-Gly-Asp-Phe-Glu-Glu-Ile-Glu-Glu-Tyr-Leu-Gln-OH wherein X=Suc, $A_1$=Gly-Asp, $A_2$=Phe, $A_3$=Glu, $A_4$=Glu, $A_5$=Ile, $A_6$=a bond, $A_7$=Glu, $A_8$=Glu, $A_9$=Tyr-Leu, $A_{10}$=Gln, and Y is a carboxy terminal substituent that is OH.

17. A compound of the structure Suc-Tyr-Glu-Pro-Tiq-Glu-Glu-Ala-Cha-D-Glu-OH.

18. A compound of the structure Suc-Tyr-Glu-Pro-Ile-Pro-Glu-Glu-Ala-Gln-$NH_2$.

19. A compound of the structure Suc-Tyr-Glu-Pro-Ile-Pro-Glu-Glu-Cha-Gln-$NH_2$.

20. A compound of the structure Suc-Tyr-Glu-Pro-Ile-Pro-Glu-Ala-Cha-Asn-OH.

21. A compound of the structure Suc-Tyr-Glu-Pro-Ile-Pro-Glu-Glu-Ala-Asn-OH.

22. A compound of the structure Mal-Tyr-Pro-Ile-Pro-Glu-Glu-Ala-Cha-D-Glu-OH wherein X=Mal $A_1$=a bond, $A_2$=Tyr, $A_3$=a bond, $A_4$=Pro, $A_5$=Ile, $A_6$=Pro, $A_7$=Glu, $A_8$=Glu, $A_9$=Ala-Cha, $A_{10}$=D-Glu, and Y is a carboxy terminal substituent that is OH.

23. A compound of claim 1 of the structure Suc-Nap-Pro-Ile-Pro-Glu-Glu-Ala-Cha-D-Glu-OH wherein X=Suc, $A_1$=a bond, $A_2$=Nap, $A_3$=a bond, $A_4$=Pro, $A_5$=Ile, $A_6$=Pro, $A_7$=Glu, $A_8$=Glu, $A_9$=Ala-Cha, $A_{10}$=D-Glu, and Y is a carboxy terminal substituent that is OH.

24. A compound of claim 1 of the structure Suc-Tyr-Glu-Ile-Pro-Glu-Glu-Ala-Cha-D-Glu-OH wherein X=Suc, $A_1$=a bond, $A_2$=Tyr, $A_3$=Glu, $A_4$=a bond, $A_5$=Ile, $A_6$=Pro, $A_7$=Glu, $A_8$=Glu, $A_9$=Ala-Cha, $A_{10}$=D-Glu, and Y is a carboxy terminal substituent that is OH.

25. A compound claim 1 of the structure Suc-Tyr-Glu-Pro-Pro-Glu-Glu-Ala-Cha-D-Glu-OH wherein X=Suc, $A_1$=a bond, $A_2$=Tyr, $A_3$=Glu, $A_4$=Pro, $A_5$=a bond, $A_6$=Pro, $A_7$=Glu, $A_8$=Glu, $A_9$=Ala-Cha, $A_{10}$=D-Glu, and Y is a carboxy terminal substituent that is OH.

26. A compound of claim 1 of the structure Suc-Tyr-Glu-Pro-Ile-Glu-Glu-Ala-Cha-D-Glu-OH wherein X=Suc, $A_1$=a bond, $A_2$=Tyr, $A_3$=Glu, $A_4$=Pro, $A_5$=Ile, $A_6$=a bond, $A_7$=Glu, $A_8$=Glu, $A_9$=Ala-Cha, $A_{10}$=D-Glu, and Y is a carboxy terminal substituent that is OH.

27. A compound of claim 1 of the structure Suc-Tyr-Glu-Pro-Ile-Pro-Glu-Ala-Cha-D-Glu-OH wherein X=Suc, $A_1$=a bond, $A_2$=Tyr, $A_3$=Glu, $A_4$=Pro, $A_5$=Ile, $A_6$=Pro, $A_7$=Glu, $A_8$=a bond, $A_9$=Ala-Cha, $A_{10}$=D-Glu, and Y is a carboxy terminal substituent that is OH.

28. A compound of the structure Suc-Tyr-Glu-Pro-Ile-Pro-Glu-Glu-Ala-D-Glu-OH.

29. A compound of the structure Suc-Tyr-Glu-Pro-Ile-Pro-Glu-Glu-Cha-D-Glu-OH.

30. A compound of one of claims 1 of the structure Suc-Tyr-Glu-Pro-Ile-Pro-Glu-Glu-Ala-Gln-OH.

31. A compound of the structure Suc-Phe-Glu-Pro-Ile-Pro-Glu-Glu-Ala-Gln-$NH_2$.

32. A compound of the structure Suc-Tyr-Glu-Pro-Ile-Pro-Glu-Glu-Ala-Cha-OH.

33. A compound of the structure Suc-Glu-Pro-Ile-Pro-Glu-Glu-Ala-Cha-D-Glu-OH.

34. A compound of one of claims 1, or 15–33 that is useful as an anticoagulant agent.

* * * * *

UNITED STATES PATENT AND TRADEMARK OFFICE
CERTIFICATE OF CORRECTION

PATENT NO. : 5,192,747
DATED : March 9, 1993
INVENTOR(S) : John L. Krstenansky

It is certified that error appears in the above-indentified patent and that said Letters Patent is hereby corrected as shown below:

Column 7, line 33, "u-amino" should read-- "a-amino".
Column 8, line 21, "u-amino" should read--"a-amino".
Column 9, line 51, "anticoaqulant" should read--"Anticoaqulant".
Column 13, claim 1, line 21, "$A_6$ is a bond, [Tiq,] Pro," should read--
"$A_6$ is a bond, Pro,".

Signed and Sealed this

Twenty-sixth Day of April, 1994

Attest:

BRUCE LEHMAN

*Attesting Officer*   *Commissioner of Patents and Trademarks*